(12) United States Patent
Liu et al.

(10) Patent No.: US 10,934,552 B2
(45) Date of Patent: Mar. 2, 2021

(54) CONSTRUCTION AND APPLICATION OF ENGINEERING BACTERIA CAPABLE OF SECRETING AND EXPRESSING DIACETYLCHITOBIOSE DEACETYLASE

(71) Applicants: Jiangnan University, Wuxi (CN); SHANDONG RUNDE BIOTECHNOLOGY CO., LTD, Xintai (CN)

(72) Inventors: Long Liu, Wuxi (CN); Jian Chen, Wuxi (CN); Guocheng Du, Wuxi (CN); Xueqin Lv, Wuxi (CN); Jianghua Li, Wuxi (CN); Zhu Jiang, Wuxi (CN); Wei Lu, Xintai (CN); Hongzhi Zhang, Xintai (CN); Jianxing Lu, Xintai (CN); Changfeng Liu, Xintai (CN)

(73) Assignees: Jiangnan University, Wuxi (CN); SHANDONG RUNDE BIOTECHNOLOGY CO., LTD, Xintai (CN)

(*) Notice: Subject to any disclaimer, the term of this patent is extended or adjusted under 35 U.S.C. 154(b) by 0 days.

(21) Appl. No.: 16/503,699

(22) Filed: Jul. 5, 2019

(65) Prior Publication Data
US 2020/0291410 A1   Sep. 17, 2020

(30) Foreign Application Priority Data
Mar. 14, 2019   (CN) .......................... 201910193636.5

(51) Int. Cl.
*C12N 15/75*   (2006.01)
*C12N 1/20*    (2006.01)
*C12N 9/80*    (2006.01)
*A61K 31/7008* (2006.01)
*A23L 29/30*   (2016.01)

(52) U.S. Cl.
CPC .............. *C12N 15/75* (2013.01); *A23L 29/30* (2016.08); *A61K 31/7008* (2013.01); *C12N 1/20* (2013.01); *C12N 9/80* (2013.01); *C12N 2500/12* (2013.01); *C12N 2500/74* (2013.01)

(58) Field of Classification Search
None
See application file for complete search history.

(56) References Cited

PUBLICATIONS

Guan et al.,"Construction of a highly active secretory expression system via an engineered dual promoter and a highly efficient signal peptide in Bacillus subtilis", New Biotechnology 33(3): 372-379 (May 2016). (Year: 2016).*

* cited by examiner

*Primary Examiner* — Anand U Desai
(74) *Attorney, Agent, or Firm* — IPro, PLLC

(57) ABSTRACT

The disclosure herein relates to construction and application of engineering bacteria capable of secreting and expressing diacetylchitobiose deacetylase, and belongs to the technical field of fermentation engineering. Firstly, recombinant *B. subtilis* capable of heterologously secreting and expressing a diacetylchitobiose deacetylase gene is constructed, and a signal peptide fragment yncM is added into the recombinant vector for the first time. The signal peptide can secrete the target protein diacetylchitobiose deacetylase outside the cells of the recombinant *B. subtilis*, and a mutant of the 5'-end untranslated region is acquired, thereby significantly increasing the expression level of the target protein, and greatly simplifying the subsequent enzyme separation and purification steps. When the acquired diacetylchitobiose deacetylase is fermented and cultured in a fermentation medium for 50-60 h, the enzyme activity reaches a maximum of 1,548.7 U/mL, and the maximum yield of the diacetylchitobiose deacetylase is about 620 mg/L. Simultaneously, the method has the advantages of low production cost, mild production conditions, simple purification process steps, safe production operation and the like.

15 Claims, 6 Drawing Sheets
Specification includes a Sequence Listing.

CONSTRUCTION AND APPLICATION OF ENGINEERING BACTERIA CAPABLE OF SECRETING AND EXPRESSING DIACETYLCHITOBIOSE DEACETYLASE

REFERENCE TO SEQUENCE LISTING SUBMITTED VIA EFS-WEB

Pursuant to the EFS-Web legal framework and 37 CFR §§ 1.821-825 (see MPEP § 2442.03(a)), a Sequence Listing in the form of an ASCII-compliant text file (entitled "Seq.txt" created on Mar. 14, 2019, and 16,600 bytes in size) was submitted concurrently with the instant application, and the entire contents of the Sequence Listing are incorporated herein by reference in its entirety.

TECHNICAL FIELD

The disclosure herein relates to construction and application of engineering bacteria capable of secreting and expressing diacetylchitobiose deacetylase, and belongs to the technical field of fermentation engineering.

BACKGROUND

Diacetylchitobiose deacetylase is derived from *Pyrococcus horikoshii* OT3 and is a key enzyme in processes of biodegrading chitin and chitosan, and producing chitosan oligosaccharides and chitosan monosaccharides. Among them, diacetylchitobiose deacetylase has high activity on acetylglucosamine monomer and can be used to produce glucosamine. Glucosamine plays an important role in repairing and maintaining cartilage and joint tissue functions, is a kind of medicine with high recognition degree in the world for effectively reducing the incidence of osteoarthritis, and can effectively relieve the osteoarthritis when used as a dietary supplement. In addition, diacetylchitobiose deacetylase plays an important role in the metabolic pathway of chitin in *Pyrococcus horikoshii* OT3. The enzyme is derived from *Pyrococcus horikoshii* OT3 and therefore has extreme heat resistance and good thermal stability. However, the growth conditions in the *Pyrococcus horikoshii* OT3 are demanding and the culture cost is high, so development of a simple, environment-friendly and efficient method for producing chitobiose is urgently needed.

At present, diacetylchitobiose deacetylase of different sources have been expressed in *E. coli* for studying the degradation mechanism of chitin. However, diacetylchitobiose deacetylase overexpressed by plasmids accumulates in a large amount in the form of inclusion bodies, and soluble recombinant protein can be produced by inserting the target gene into *E. coli* chromosome or using *B. subtilis* as a host, and performing intracellular expression of the enzyme, but the output is still very low. Expression of the diacetylchitobiose deacetylase by these methods still has shortcomings such as low expression level, requirement for cell wall breaking for acquiring pure enzyme, and complicated purification steps, and the yield of soluble protein is lower than 40 mg/L. Therefore, it is necessary to use modern bioengineering technology and fermentation engineering methods to increase the expression of enzymes to meet the needs of many fields. At present, there is no report on secretion and expression of diacetylchitobiose deacetylase. Extracellular production of the enzyme greatly simplifies the subsequent protein purification process, and eliminates the need for complicated extraction processes such as cell disruption and protein refolding. Moreover, the special heat resistance and thermal stability of the diacetylchitobiose deacetylase can simplify the downstream purification process and significantly reduce the production cost of pure enzyme.

*Bacillus subtilis* (*B. subtilis*) is a production host widely used as a food enzyme preparation and an important nutrient chemical. Its products are certified by the FDA as "generally regarded as safe" (GRAS). *B. subtilis* is widely used as an expression host for enzymes and antibiotics in industrial production due to its non-pathogenicity, safety, no obvious codon bias, easy separation and purification of metabolites, and other advantages; it has clear genetic background and is easy for genetic engineering operation; it is safe and free of toxins, and has no threat to organisms and the environment; it can carry out secretion and expression and is easy to purify; a fermentation process is simple and the raw material cost is low. Therefore, a *B. subtilis* bacterial strain capable of highly secreting and expressing diacetylchitobiose deacetylase has good economic and social benefits.

SUMMARY

The first object of the disclosure is to provide genetic engineering bacteria which fuse and express diacetylchitobiose deacetylase and a yncM signal peptide, and introduce a DNA fragment comprising SEQ ID NO. 3 into a 5'-untranslated region of a diacetylchitobiose deacetylase gene.

In one embodiment of the disclosure, the Genbank accession number of the diacetylchitobiose deacetylase is PH0499.

In one embodiment of the disclosure, the amino acid sequence of the yncM signal peptide is as shown in SEQ ID NO. 5, and the nucleotide sequence is as shown in SEQ ID NO. 1.

In one embodiment of the disclosure, the genetic engineering bacteria take p43NMK as a vector.

In one embodiment of the disclosure, the genetic engineering bacteria take *B. subtilis* WB600 as a host.

In one embodiment of the disclosure, the gene sequence encoding the diacetylchitobiose deacetylase is as shown in SEQ ID NO. 2.

The second object of the disclosure is to provide a method for preparing the diacetylchitobiose deacetylase by applying the genetic engineering bacteria to fermentation.

In one embodiment of the disclosure, the genetic engineering bacteria are cultured in an LB medium, and the culture conditions are 35-37° C., 200-220 rpm, and 10-15 h to obtain a seed solution; the seed solution is inoculated into a TB fermentation medium according to an inoculum concentration of 2-5%, and the culture conditions are 35-37° C., 200-220 rpm, and 14-96 h.

The LB medium is a conventional medium in the art, and the composition per liter comprises: peptone 10 g, yeast powder 5 g, and NaCl 10 g.

The TB medium is a conventional medium in the art, and the composition per liter comprises: peptone 12 g, yeast powder 24 g, NaCl 10 g, glycerol 4 mL, $KH_2PO_4$ 2.31 g, and $K_2HPO_4$ 12.54 g.

The third object of the disclosure is to provide a construction method of the genetic engineering bacteria, comprising: fusing diacetylchitobiose deacetylase and a yncM signal peptide, introducing a mutant sequence SEQ ID NO. 3 into a 5'-untranslated region of a diacetylchitobiose deacetylase gene, finally connecting the acquired complete fragment with a vector, and transferring into *B. subtilis* to obtain the genetic engineering bacteria.

The fourth object of the disclosure is to provide application of the genetic engineering bacteria to preparation of a drug or a dietary supplement.

The fifth object of the disclosure is to provide application of the genetic engineering bacteria in preparation of glucosamine.

Firstly, recombinant *B. subtilis* capable of heterologously secreting and expressing a diacetylchitobiose deacetylase gene is constructed, and a signal peptide fragment yncM is added into the recombinant vector for the first time. The signal peptide can secrete the target protein diacetylchitobiose deacetylase outside the cells of the recombinant *B. subtilis*, and a mutant of the 5'-end untranslated region is acquired, thereby significantly increasing the expression level of the target protein, and greatly simplifying the subsequent enzyme separation and purification steps. When the acquired diacetylchitobiose deacetylase is fermented and cultured in a fermentation medium for 50-60 h, the enzyme activity reaches a maximum of 1,548.7 U/mL, and the maximum yield of the diacetylchitobiose deacetylase is about 620 mg/L. Simultaneously, the method has the advantages of low production cost, mild production conditions, simple purification process steps, safe production operation and the like.

BRIEF DESCRIPTION OF FIGURES

FIG. 5 is a comparison diagram of extracellular enzyme before and after mutation of a 5'-untranslated region, wherein

Figure 1:
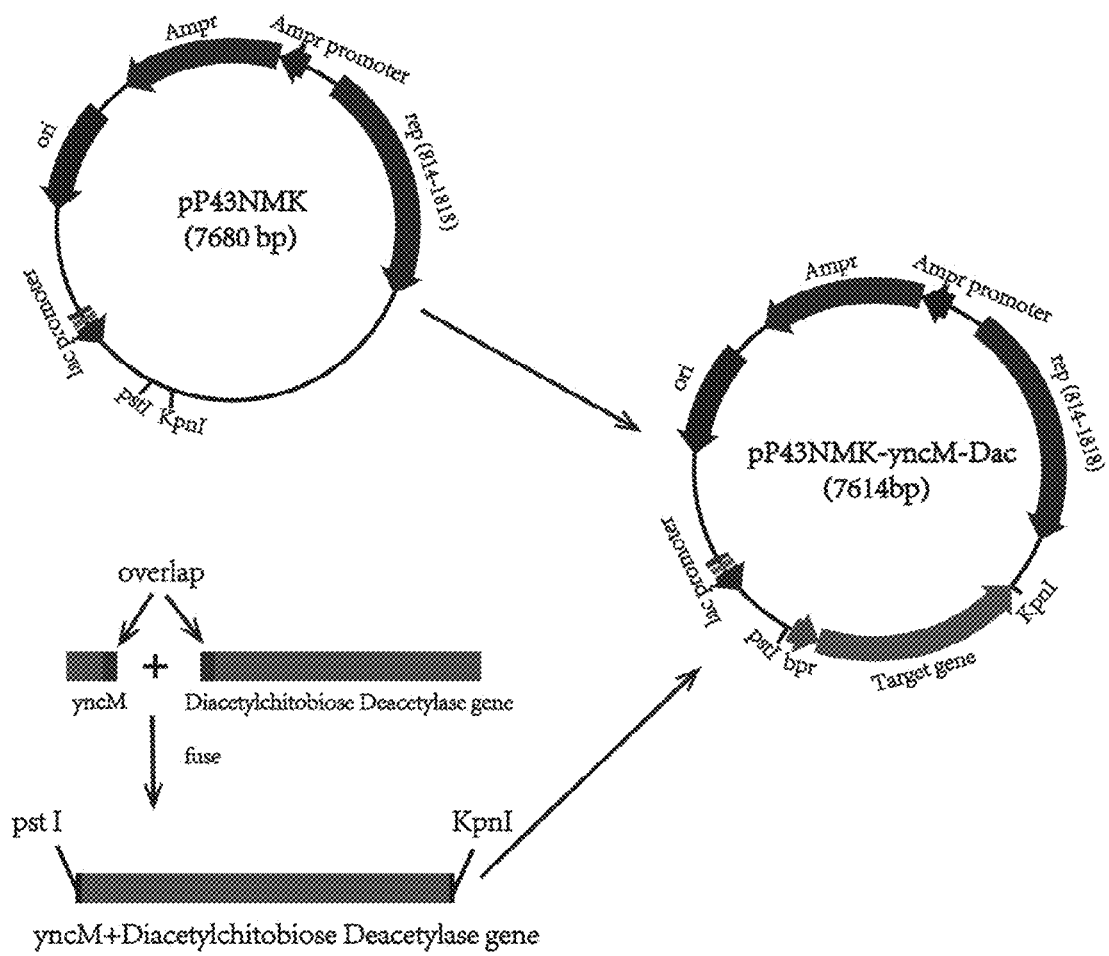
FIG. 1 is a recombinant plasmid construction diagram.

DETAILED DESCRIPTION (1) Bacterial Strains and Vectors

The plasmid is replicated by using *Escherichia coli* JM109 as a host strain, and the expression of deacetylase and fermentation of the strain are carried out by *B. subtilis* WB600. The plasmid pP43NMK is a commercial plasmid.

(2) Reagents, Enzymes and Related Kits

Antibiotics (kanamycin sulfate and ampicillin) are purchased from Sangon Biotech (Shanghai) Co., Ltd.

All kinds of chemical reagents are of analytical grade and are purchased from Shanghai Sinopharm Group.

All kinds of restrictive enzymes and DNA ligases are purchased from Takara.

1 kb DNA Ladder and a plasmid miniprep kit are purchased from Sangon Biotech (Shanghai) Co., Ltd. A gel recovery kit is purchased from Fermentas.

(3) Media

The composition of a seed medium per 100 mL comprises: peptone 1 g, yeast powder 0.5 g, and NaCl 1 g.

The composition of a fermentation medium per 100 mL comprises: peptone 1.2 g, yeast powder 2.4 g, glycerol 0.4 mL, $KH_2PO_4$ 0.23 g, and $K_2HPO_4$ 1.25 g.

(4) HPLC Determination Method

Preparation of an HPCL sample to be tested: 1 mL of reaction solution is taken, precipitate in the reaction is removed by centrifugation, and an appropriate amount of the supernatant is taken, diluted properly with deionized water, and filtered through a membrane with a pore size of 0.22 μm. The filtrate is subjected to analysis by high performance liquid chromatography.

Determination of acetylglucosamine content: an Agilent 1260 high performance liquid chromatograph (with a differential detector) and an HPX-87H column (Bio-Rad, Hercules, Calif.) are used; 0.5 mM dilute sulfuric acid is used as a mobile phase; the flow rate is 0.6 mL/min; the sample size is 10 μL; the column temperature is 40° C.; isocratic elution is carried out. Detection is carried out by the differential detector.

Determination of glucosamine content: an Agilent 1260 high performance liquid chromatograph (with a UV-visible detector) and an Agilent ODS (250 mm×4.6 mm, 5 μm) chromatographic column are used; a derivatization reagent is OPA (o-phthaldialdehyde); a mobile phase A is prepared by weighing 3.02 g of anhydrous sodium acetate in a beaker, adding deionized water to dissolve the anhydrous sodium acetate and dilute to 1 L, then adding 200 μL of triethylamine, adjusting the PH to 7.20±0.05 with 5% acetic acid, and after suction filtration, adding 5 ml of tetrahydrofuran and carrying out mixing for later use; a mobile phase B is prepared by weighing 3.02 g of anhydrous sodium acetate in a beaker, adding deionized water to dissolve the anhydrous sodium acetate and enabling the constant volume to be 200 mL, adjusting the pH to 7.20±0.05 with 5% acetic acid, and after suction filtration, adding 400 mL of acetonitrile and 400 mL of methanol to the solution and carrying out mixing for later use; the flow rate is 1.0 mL/min; the sample size is 20 μL; the column temperature is 40° C.; gradient elution is carried out. Detection is carried out by the UV detector at a detection wavelength of 330 nm.

(5) Definition and Determination Method of Enzyme Activity Unit

At 40° C., with 50 mM pH 8.0 PB as a buffer, the enzyme amount, which can convert 1 μmol of substrate acetylglucosamine to 1 μmol of product glucosamine in 1 h, is called an enzyme activity unit, i.e., 1 U=1 μmol/h.

Determination method of enzyme activity of diacetylchitobiose deacetylase:

5 mL of acetylglucosamine solution is accurately sucked and added into clean test tubes 1# and 2# with stoppers respectively, and preheated for 5 minutes in a 40° C. water bath kettle; 5 mL of crude enzyme solution is added to the test tube 2# (the enzyme solution is appropriately diluted with a pH 8.0 PB buffer, and the dilution factor is N), and 5 mL of PB solution is added to the test tube 1#; the mixed solutions are shaken intermittently for 2 min in a 40° C. constant temperature water bath; after taking out, 1 mL of 1 M dilute hydrochloric acid solution is immediately added to each of the test tubes 1# and 2# to terminate the reaction. The mixed solutions are subjected to external standard detection analysis by liquid chromatography.

Drawing of a standard curve: an acetylglucosamine standard (with accuracy of 0.0001 g) is accurately weighed to prepare 1 g/L, 2 g/L, 3 g/L, 4 g/L and 5 g/L acetylglucosamine solutions, liquid phase detection is carried out and a standard curve is drawn.

Calculation of enzyme activity:

$$X = \frac{(A-B) \times 1.1 \times (5+5)}{215.6 \times 2 \times 5} \times 10^3 \times N \times 60$$

where X—Enzyme activity, U/mL;
5—Volume of an enzyme solution, mL;
5—Volumic number of a substrate solution (100 g/L acetylglucosamine solution), mL;
A—Glucosamine content of reaction liquid, g/L;
B—Glucosamine content of blank liquid, g/L;
N—Dilution rate of the enzyme solution;
1.1—Dilution rate of a sample after a terminator is added;
215.6—Molar mass of standard sample glucosamine hydrochloride, g/mol;
5—Volumic number of a substrate solution (100 g/L acetylglucosamine solution), mL;
2—Reaction time, min;
60—1 h is 60 min.

Biochemical techniques used in the disclosure are all conventional techniques in the art.

Example 1 Construction of Recombinant Plasmids which Secrete and Express Diacetylchitobiose Deacetylase A gene encoding a signal peptide yncM (with the nucleotide sequence as shown in SEQ ID NO. 1) and a gene encoding diacetylchitobiose deacetylase Dac (with the nucleotide sequence as shown in SEQ ID NO. 2), namely two target genes are inserted into an expression vector pP43NMK by seamless cloning (the insertion sites are KpnI and PstI), and a recombinant plasmid pP43NMK-yncM-Dac is constructed (as shown in FIG. 1).

Example 2 Acquisition of 5'-Untranslated Region Mutants

Figure 2:
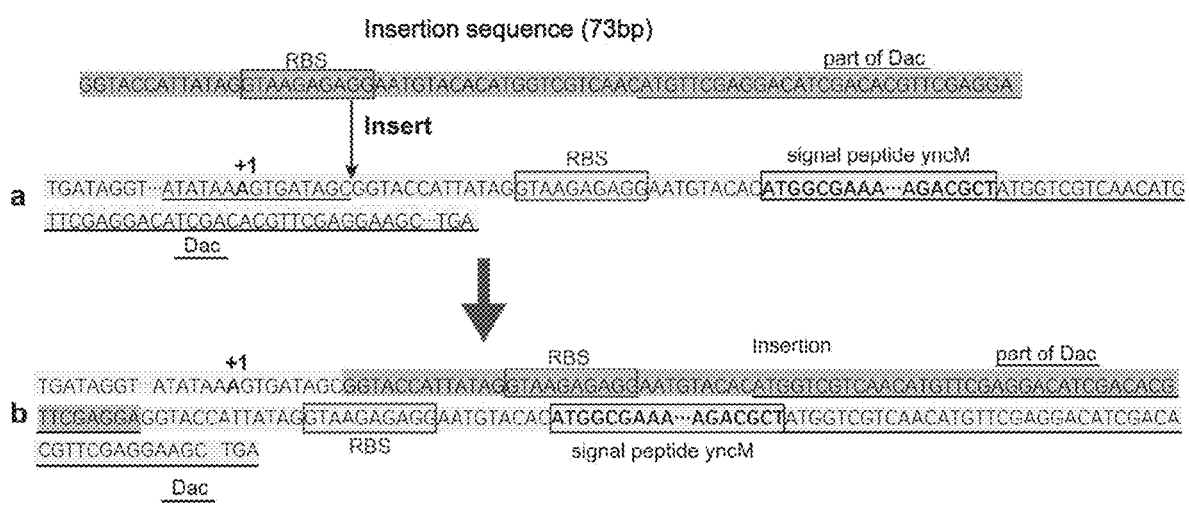
FIG. 2 is a comparison diagram of the sequence of a 5'-untranslated region before and after mutation; a is the sequence of the 5'-untranslated region of a plasmid pP43NMK-yncM-Dac before mutation (SEQ ID NO:17); b is the sequence of the 5'-untranslated region of the mutant plasmid pP43mut-yncM-Dac acquired after sequence insertion (SEQ ID NO:18); "Insertion sequence (73 bp)" corresponds to SEQ ID NO:3.

In the process of constructing the recombinant plasmid pP43NMK-yncM-Dac in Example 1, a 5'-untranslated region mutant is acquired and found to have a 73 bp base insertion at the 5'-end by sequencing and analyzing (as shown in FIG. 2), and the mutated recombinant plasmid is named pP43mut-yncM-Dac (with the nucleotide sequence as shown in SEQ ID NO. 4).

Example 3 Construction of Recombinant B. subtilis

The recombinant plasmid pP43mut-yncM-Dac acquired in Example 2 is transformed into a cloning host E. coli JM109, and single colonies growing on an LB kanamycin resistant plate are picked for colony PCR identification; positive clones are cultured for extracting plasmids and the plasmids are subjected to double enzyme digestion identification, correct digestion bands are selected for sequencing, and the recombinant plasmid with a correct sequencing result is transformed into an expression host B. subtilis WB600.

Example 4 Secretion and Expression of Diacetylchitobiose Deacetylase Encoding Gene in B. subtilis WB600

The recombinant B. subtilis bacterial strain acquired in Example 3 is inoculated into a seed medium containing kanamycin antibiotics (10 mg/L) at 37° C., and cultured overnight at 220 rpm with shaking. Transferring is carried out to a fresh fermentation medium containing kanamycin antibiotics (10 mg/L) according to an inoculum concentration (v/v) of 4%, and cultured for 14-80 h at 37° C. at 220 rpm with shaking. The enzyme activity reaches a maximum of 1,548.7 U/mL during fermentation, and the yield of diacetylchitobiose deacetylase reaches a maximum of 620 mg/L.

Example 5 Growth of Recombinant B. subtilis

Figure 3:
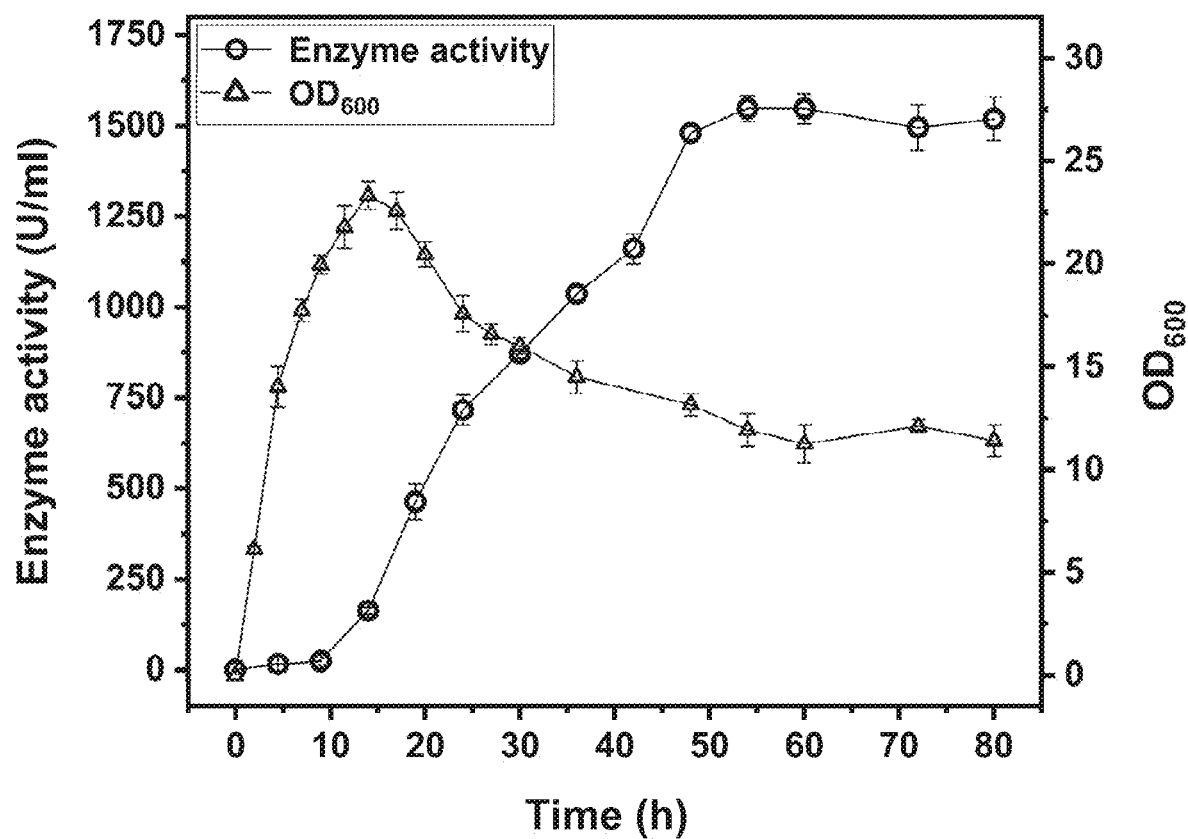
FIG. 3 is an enzyme activity curve and a thallus growth curve of diacetylchitobiose deacetylase at different fermentation stages.

The recombinant B. subtilis bacterial strain acquired in Example 3 is inoculated into a seed medium containing kanamycin antibiotics (10 mg/L) at 37° C., and cultured overnight at 220 rpm with shaking. Transferring is carried out to a fresh fermentation medium containing kanamycin antibiotics (10 mg/L) according to an inoculum concentration (v/v) of 4%, and cultured at 37° C. at 220 rpm with shaking. Samples are taken every 2-8 h and diluted appropriately with deionized water, and $OD_{600}$ is measured with an ultraviolet spectrophotometer to plot the growth curve of the thallus. As shown in FIG. 3, after 12 h, the growth of the thallus enters an equilibrium phase, the concentration of the thallus reaches the highest at 14 h ($OD_{600}$=23.3), and begins to decrease at around 18 h, and then the growth of the thallus enters a decline phase.

Example 6 Detection of Enzyme Activity of Diacetylchitobiose Deacetylase in B. subtilis WB600 at Different Stages Samples are taken from different fermentation stages and centrifuged at 8,000×g, the thallus is discarded, and the supernatant is obtained, which is the crude enzyme solution. The enzyme activity is determined according to the above enzyme activity detection method. The degradation rate of acetylglucosamine is controlled at 10% or below in the detection process. Otherwise, the enzyme solution needs to be appropriately diluted with a pH 8.0 PB buffer with a concentration of 50 mM, and then the enzyme activity is determined as described above. A curve of enzyme activity over time is plotted based on the determination results. As shown in FIG. 3, the diacetylchitobiose deacetylase in the fermentation supernatant has only weak enzyme activity in earlier stages of a lag phase and a log phase, and is detected to have obvious extracellular enzyme activity when entering a balancer; when the growth enters a decline phase, the activity of diacetylchitobiose deacetylase in the fermentation supernatant increases significantly; after 48 h, the extracellular enzyme activity increases slowly, reaches the peak at 60 h (1,548.7 U/mL), and then basically stabilizes.

Control 1

Figure 4:
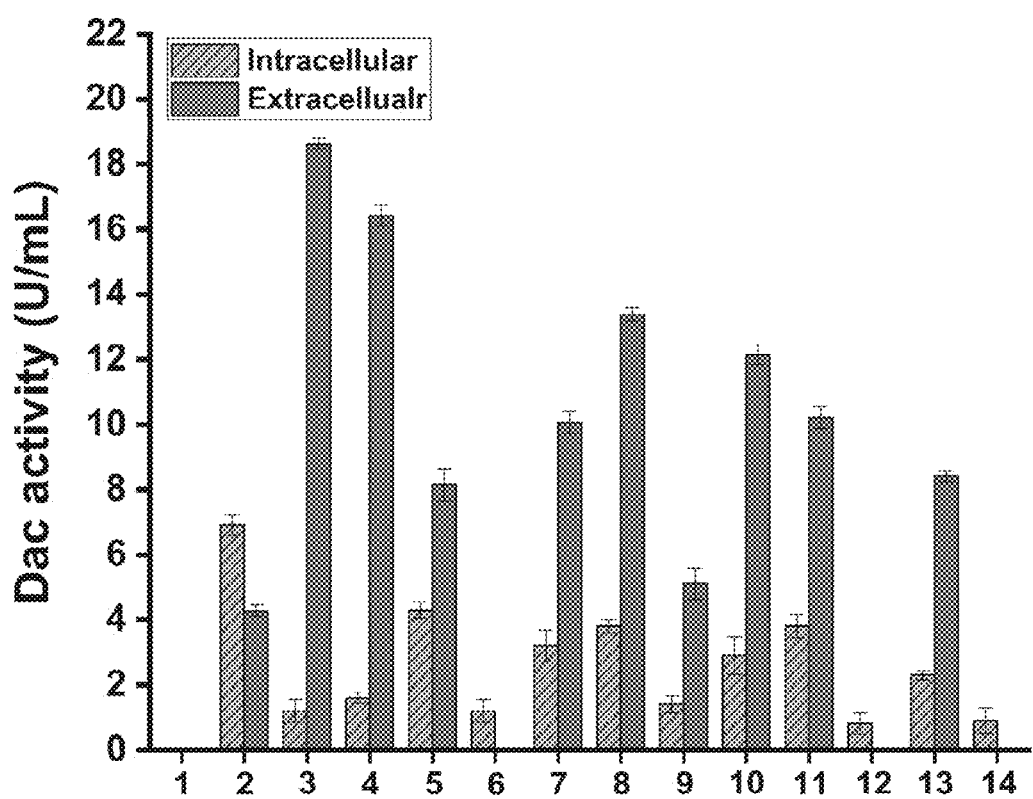
FIG. 4 is a bar diagram of the activity of diacetylchitobiose deacetylase containing different signal peptides, wherein 1 is free of Dac gene; 2 contains Dac gene but is free of signal peptide; 3 contains Dac gene and yncM signal peptide; 4 contains Dac gene and bpr signal peptide; 5 contains Dac gene and ywbN signal peptide; 6 contains Dac gene and ansZ signal peptide; 7 contains Dac gene and yvgO signal peptide; 8 contains Dac gene and amyE signal peptide; 9 contains Dac gene and oppA signal peptide; 10 contains Dac gene and vpr signal peptide; 11 contains Dac gene and lipA signal peptide; 12 contains Dac gene and wapA signal peptide; 13 contains Dac gene and Epr signal peptide; 14 contains Dac gene and yclQ signal peptide.

Plasmids fused with different signal peptides (yncM, bpr, ywbN, ansZ, yvgO, amyE, oppA, vpr, lipA, wapA, Epr and yclQ, with amino acid sequences shown in Table 1) are used as controls, and other conditions are the same as those in Examples 1-6. In the fermentation process, the plasmids fused with different signal peptides have enzyme activity ranging from 0 U/mL to 18.6 U/mL, and extracellular enzyme activity is as high as 18.6 U/mL, as shown in FIG. 4.

TABLE 1

Sequences of signal peptides

| Name | Amino acid sequences of signal peptides | SEQ ID NO: |
|---|---|---|
| yncM | MAKPLSKGGILVKKVLIAGAVGTAVLFGTLSSGIPGLPAADAQVAKA | 5 |
| bpr | MRKKTKNRLISSVLSTVVISSLLFPGAAGA | 6 |
| ywbN | MSDEQKKPEQIHRRDILKWGAMAGAAVA | 7 |
| ansZ | MKKQRMLVLFTALLFVFTGCSHS | 8 |
| yvgO | MKRIRIPMTLALGAALTIAPLSFASA | 9 |

TABLE 1-continued

Sequences of signal peptides

| Name | Amino acid sequences of signal peptides | SEQ ID NO: |
|---|---|---|
| amyE | MFAKRFKTSLLPLFAGFLLLFHLVLAGPAAASA | 10 |
| oppA | MKKRWSIVTLMLIFTLVLSA | 11 |
| vpr | MKKGIIRFLLVSFVLFFALSTGITGVQA | 12 |
| lipA | MKFVKRRIIALVTILMLSVTSLFALQPSAKA | 13 |
| wapA | MKKRKRRNFKRFIAAFLVLALMISLVPADVLA | 14 |
| Epr | MKNMSCKLVVSVTLFFSFLTIGPLAHA | 15 |
| yclQ | MKKFALLFIALVTAVVISACGNQSTSSKG | 16 |

Control 2

Figure 5A:
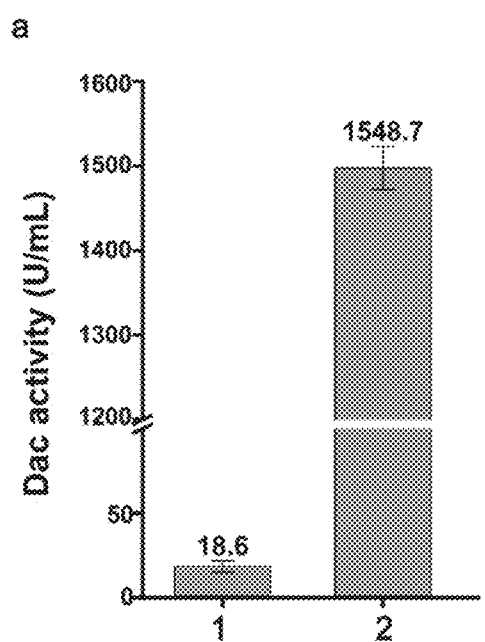
FIG. 5A is the difference of extracellular enzyme activity before and after mutation of the 5'-untranslated region.
Figure 5B:
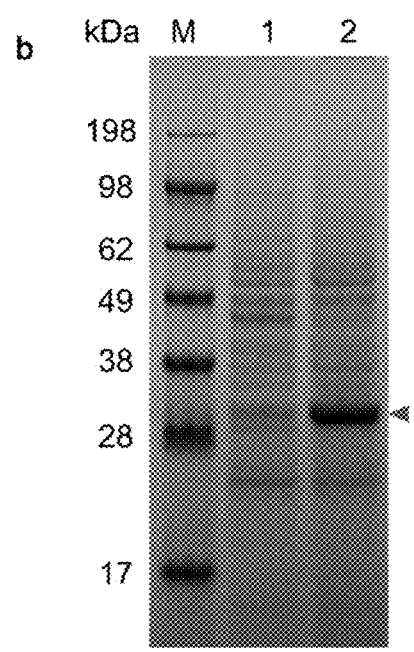
FIG. 5B is a protein gel diagram of extracellular enzyme content in fermentation supernatant before and after mutation of the 5'-untranslated region; M is molecular weight protein standard; 1 is pP43NMK-yncM-Dac; 2 is pP43mut-yncM-Dac.

The recombinant plasmid pP43NMK-yncM-Dac which is not mutated in the 5'-untranslated region is used as a control, and other conditions are the same as those in Examples 1-6. The enzyme activity reaches a maximum of 18.6 U/mL during fermentation, and the yield of diacetylchitobiose deacetylase reaches a maximum of 12 mg/L, as shown in FIG. 5.

What is claimed is:

1. A genetically engineered bacterium, comprising an expression vector encoding a diacetylchitobiose deacetylase gene fused downstream to a yncM signal peptide, wherein the diacetylchitobiose deacetylase gene harbors a DNA fragment comprising SEQ ID NO:3 in a 5'-untranslated region of the diacetylchitobiose deacetylase gene.

2. The bacterium according to claim 1, wherein the diacetylchitobiose deacetylase GenBank accession number is PH0499.

3. The bacterium according to claim 1, wherein an amino acid sequence of the yncM signal peptide is SEQ ID NO:5.

4. The bacterium according to claim 3, wherein a nucleotide sequence that encodes the yncM signal peptide is SEQ ID NO:1.

5. The bacterium according to claim 1, wherein the expression vector is p43NMK.

6. The bacterium according to claim 1, wherein the bacterium is *B. subtilis*.

7. The bacterium according to claim 6, wherein the *B. subtilis* is strain WB600.

8. A method of producing diacetylchitobiose deacetylase, comprising:
inserting into a host bacterium an expression vector encoding a diacetylchitobiose deacetylase gene fused downstream to a yncM signal peptide, wherein the diacetylchitobiose deacetylase gene harbors a DNA fragment comprising SEQ ID NO:3 in a 5'-untranslated region of the diacetylchitobiose deacetylase gene,
inoculating a fermentation culture with the bacterium,
incubating the culture under conditions that favor expression of the diacetylchitobiose deacetylase, and
obtaining diacetylchitobiose deacetylase from the culture.

9. The method according to claim 8, wherein inoculating the bacterium into the fermentation culture comprises inoculating a concentration of 2-5% of the bacterium into the culture, and wherein incubating is performed under conditions of 35 to 37° C. and shaking at 200 to 220 rpm for 14 to 96 hours.

10. The method according to claim 8, wherein wherein incubating is performed under conditions of 35 to 37° C. and shaking at 200 to 220 rpm for 10 to 15 hours.

11. The method according to claim 8, wherein the fermentation culture per liter comprises: 12 grams of peptone, 24 grams of yeast powder, 10 grams NaCl, 4 mL glycerol, 2.31 grams $KH_2PO_4$ and 12.54 grams $K_2HPO_4$.

12. The method according to claim 8, wherein the fermentation culture per liter comprises: 10 grams peptone, 5 grams yeast powder, and 10 grams NaCl.

13. A method of preparing glucosamine, comprising:
providing a genetically engineered bacterium comprising an expression vector encoding a diacetylchitobiose deacetylase gene downstream of a yncM signal peptide, and harboring a DNA fragment comprising SEQ ID NO:3 in a 5'-untranslated region of the diacetylchitobiose deacetylase gene,
inoculating a fermentation culture with the bacterium, and
incubating the culture under conditions sufficient to express diacetylchitobiose deacetylase, thereby producing diacetylchitobiose deacetylase, and incubating the diacetylchitobiose deacetylase with acetyl-glucosamine to produce glucosamine.

14. The method according to claim 13, which further comprises adding the glucosamine to a composition comprising a drug.

15. The method according to claim 13, which further comprises adding the glucosamine to a dietary supplement.

\* \* \* \* \*

SEQUENCE LISTING

```
<160> NUMBER OF SEQ ID NOS: 18

<210> SEQ ID NO 1
<211> LENGTH: 126
<212> TYPE: DNA
<213> ORGANISM: Artificial Sequence
<220> FEATURE:
<223> OTHER INFORMATION: Synthetic DNA

<400> SEQUENCE: 1
atggcgaaac cactatcaaa aggggaatt  ttggtgaaaa aagtattgat tgcaggtgca      60
gtaggaacag cagttctttt cggaacccett tcatcaggta taccaggttt acccgcggca    120
gacgct                                                                126

<210> SEQ ID NO 2
<211> LENGTH: 819
<212> TYPE: DNA
<213> ORGANISM: Artificial Sequence
<220> FEATURE:
<223> OTHER INFORMATION: Synthetic DNA

<400> SEQUENCE: 2
atggtcgtca acatgttcga ggacatcgac acgttcgagg aagcgtttaa caagctgctg      60
cgcgaagtcc tggaatttga tctgcaaaat ccgttcaaag acgcgaagaa agtcctttgc    120
atcgaaccgc atccggacga ttgcgttatt ggaatgggcg gcacaatcaa aaaactgagc    180
gatatgggcg tcgaagtcat ctacgtttgc atgacagacg gctatatggg cacaacagac    240
gaaagcctgt caggacacga attagcagca atccgccgca aagaagaaga agaaagcgca    300
cgcctgctgg gcgttaaaaa gatctattgg ctgaactacc gcgatacaga actgccgtat    360
tcacgcgaag tccgcaaaga tctgacgaaa attctgcgca aagaacaacc ggacggagtt    420
tttgcaccag atccttggct tccgtacgaa tcacatccgg atcatagacg cacaggcttt    480
ctggcgattg aatcagttgc gtttagccag ctgccgaatt ttagcaacac ggatctggac    540
```

```
attggcctga atccgtataa cagcggaagc tttatcgcgc tgtactacac gcacaaaccg    600
aactacatcg tcgacatcac ggacctgatg gaactgaaac tgaaggcgat tcgcgtccat    660
agaagccagt ttccggacga tatttgggag aaatgggaac cgttcctgag aacaatcgcg    720
atgttctacg gcgaaaaaat cggcgttcgc tacggagaag ctttagaat tatgccgggc     780 ctgttctacc acatcacacc gtttacggac ctgatctga                           819
```

<210> SEQ ID NO 3
<211> LENGTH: 73
<212> TYPE: DNA
<213> ORGANISM: Artificial Sequence
<220> FEATURE:
<223> OTHER INFORMATION: Synthetic DNA

<400> SEQUENCE: 3

```
ggtaccatta taggtaagag aggaatgtac acatggtcgt caacatgttc gaggacatcg    60
acacgttcga gga                                                       73
```

<210> SEQ ID NO 4
<211> LENGTH: 7723
<212> TYPE: DNA
<213> ORGANISM: Artificial Sequence
<220> FEATURE:
<223> OTHER INFORMATION: Synthetic DNA

<400> SEQUENCE: 4

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ccttaaggaa cgtacagacg    420
gcttaaaagc ctttaaaaac gtttttaagg ggtttgtaga caaggtaaag gataaaacag    480
cacaattcca agaaaaacac gatttagaac ctaaaaagaa cgaatttgaa ctaactcata    540
accgagaggt aaaaaaagaa cgaagtcgag atcaggaat gagtttataa aataaaaaaa    600
gcacctgaaa aggtgtcttt ttttgatggt tttgaacttg ttctttctta tcttgataca    660
tatagaaata acgtcatttt tatttagtt gctgaaggt gcgttgaagt gttggtatgt    720
atgtgtttta agtattgaa acccttaaa attggttgca cagaaaaacc ccatctgtta    780
aagttataag tgactaaaca ataactaaa tagatggggg tttcttttaa tattatgtgt    840
cctaatagta gcatttattc agatgaaaaa tcaagggttt tagtggacaa gacaaaaagt    900
ggaaaagtga gaccatggag agaaaagaaa tcgctaatg ttgattactt tgaacttctg    960
catattcttg aatttaaaaa ggctgaaaga gtaaaagatt gtgctgaaat attagagtat    1020
aaacaaaatc gtgaaacagg cgaaagaaag ttgtatcgag tgtggttttg taaatccagg    1080
ctttgtccaa tgtgcaactg gaggagagca atgaaacatg gcattcagtc acaaaaggtt    1140
gttgctgaag ttattaaaca aaagccaaca gttcgttggt gtttctcac attaacagtt    1200 aaaaatgttt atgatggcga agaattaaat aagagtttgt cagatatggc tcaaggattt    1260
cgccgaatga tgcaatataa aaaaattaat aaaaatcttg ttggttttat gcgtgcaacg    1320
```

-continued

```
gaagtgacaa taaataataa agataattct tataatcagc acatgcatgt attggtatgt    1380
gtggaaccaa cttatttaa gaatacagaa aactacgtga atcaaaaaca atggattcaa    1440
ttttggaaaa aggcaatgaa attagactat gatccaaatg taaaagttca aatgattcga    1500
ccgaaaaata aatataaatc ggatatacaa tcggcaattg acgaaactgc aaaatatcct    1560
gtaaaggata cggattttat gaccgatgat gaagaaaaga atttgaaacg tttgtctgat    1620
ttggaggaag gtttacaccg taaaaggtta atctcctatg gtggtttgtt aaagaaaata    1680
cataaaaaat taaaccttga tgacacagaa gaaggcgatt tgattcatac agatgatgac    1740
gaaaaagccg atgaagatgg attttctatt attgcaatgt ggaattggga acggaaaaat    1800
tattttatta aagagtagtt caacaaacgg gccagtttgt tgaagattag atgctataat    1860
tgttattaaa aggattgaag gatgcttagg aagacgagtt attaatagct gaataagaac    1920
ggtgctctcc aaatattctt atttagaaaa gcaaatctaa aattatctga aagggaatg     1980
agaatagtga atggaccaat aataatgact agagaagaaa gaatgaagat tgttcatgaa    2040
attaaggaac gaatattgga taaatatggg gatgatgtta aggctattgg tgtttatggc    2100
tctcttggtc gtcagactga tgggccctat tcggatattg agatgatgtg tgtcatgtca    2160
acagaggaag cagagttcag ccatgaatgg acaaccggtg agtggaaggt ggaagtgaat    2220
tttgatagcg aagagattct actagattat gcatctcagg tggaatcaga ttggccgctt    2280
acacatggtc aattttctc tattttgccg atttatgatt caggtggata cttagagaaa    2340
gtgtatcaaa ctgctaaatc ggtagaagcc caaacgttcc acgatgcgat tgtgcccttt   2400
atcgtagaag agctgtttga atatgcaggc aaatggcgta atattcgtgt gcaaggaccg    2460
acaacatttc taccatcctt gactgtacag gtagcaatgg caggtgccat gttgattggt    2520
ctgcatcatc gcatctgtta tacgacgagc gcttcggtct taactgaagc agttaagcaa    2580
tcagatcttc cttcaggtta tgaccatctg tgccagttcg taatgtctgg tcaactttcc    2640
gactctgaga aacttctgga atcgctagag aatttctgga atgggattca ggagtggaca    2700
gaacgacacg gatatatagt ggatgtgtca aaacgcatac cattttgaac gatgacctct    2760
aataattgtt aatcatgttg gttacgtatt tattaacttc tcctagtatt agtaattatc    2820
atggctgtca tggcgcatta acggaataaa gggtgtgctt aaatcgggcc atttttgcgta   2880
ataagaaaaa ggattaatta tgagcgaatt gaattaataa taaggtaata gatttacatt    2940
agaaaatgaa aggggatttt atgcgtgaga atgttacagt ctatcccggc attgccagtc    3000
ggggatatta aaaagagtat aggttttat tgggataaag taggtttcac tttggttcac     3060
catgaagatg gattcgcagt tctaatgtgt aatgaggttc ggattcatct atgggaggca    3120
agtgatgaag gctggcgcct cgtagtaatg attcaccggt ttgtacaggt gcggagtcgt    3180
ttattgctgg tactgctagt tgccgcattg aagtagaggg aattgatgaa ttatatcaac    3240
atattaagcc tttgggcatt ttgcacccca atacatcatt aaaagatcag tggtgggatg    3300
aacgagactt tgcagtaatt gatcccgaca acaatttgat tagcttttt caacaaataa     3360
aaagctaaaa tctattatta atctgttcag caatcgggcg cgattgctga ataaagata     3420
cgagagacct ctcttgtatc ttttttattt tgagtggtt tgtccgttac actagaaaac     3480
cgaaagacaa taaaaatttt attcttgctg agtctggctt tcggtaagct agacaaaacg    3540
gacaaaataa aaattggcaa gggtttaaag gtggagattt tttgagtgat cttctcaaaa    3600
aatactacct gtcccttgct gatttttaaa cgagcacgag agcaaaaccc ccctttgctg    3660
aggtggcaga gggcaggttt ttttgttct ttttttctcgt aaaaaaaaga aaggtcttaa    3720
```

```
aggttttatg gttttggtcg gcactgccgc gcctcgcaga gcacacactt tatgaatata   3780
aagtatagtg tgttatactt tacttggaag tggttgccgg aaagagcgaa aatgcctcac   3840
atttgtgcca cctaaaaagg agcgatttac atatgagtta tgcagtttgt agaatgcaaa   3900
aagtgaaatc agctggacta aaaggcatgc aatttcataa tcaaagagag cgaaaaagta   3960
gaacgaatga tgatattgac catgagcgaa cacgtgaaaa ttatgatttg aaaaatgata   4020
aaatattga ttacaacgaa cgtgtcaaag aaattattga atcacaaaaa acaggtacaa    4080
gaaaaacgag gaaagatgct gttcttgtaa atgagttgct agtaacatct gaccgagatt   4140
tttttgagca actggatcct gataggtggt atgttttcgc ttgaactttt aaatacagcc   4200
attgaacata cggttgattt aataactgac aaacatcacc ctcttgctaa agcggccaag   4260
gacgctgccg ccggggctgt ttgcgttttt gccgtgattt cgtgtatcat tggtttactt   4320
attttttgc caaagctgta atggctgaaa attcttacat ttattttaca tttttagaaa    4380
tgggcgtgaa aaaagcgcg cgattatgta aaatataaag tgatagcggt accattatag    4440
gtaagagagg aatgtacaca tggtcgtcaa catgttcgag gacatcgaca cgttcgagga   4500
ggtaccatta taggtaagag aggaatgtac acatggcgaa accactatca aaaggggaa    4560
ttttggtgaa aaaagtattg attgcaggtg cagtaggaac agcagttctt ttcggaaccc   4620
tttcatcagg tataccaggt ttacccgcgg cagacgctat ggtcgtcaac atgttcgagg   4680
acatcgacac gttcgaggaa gcgttaaca agctgctgcg cgaagtcctg gaatttgatc    4740
tgcaaaatcc gttcaaagac gcgaagaaag tcctttgcat cgaaccgcat ccggacgatt   4800
gcgttattgg aatgggcggc acaatcaaaa aactgagcga tatgggcgtc gaagtcatct   4860
acgtttgcat gacagacggc tatatgggca caacagacga aagcctgtca ggacacgaat   4920
tagcagcaat ccgccgcaaa gaagaagaag aaagcgcacg cctgctgggc gttaaaaaga   4980
tctattggct gaactaccgc gatacagaac tgccgtattc acgcgaagtc cgcaaagatc   5040
tgacgaaaat tctgcgcaaa gaacaaccgg acggagtttt tgcaccagat ccttggcttc   5100
cgtacgaatc acatccggat catagacgca caggctttct ggcgattgaa tcagttgcgt   5160
ttagccagct gccgaatttt agcaacacgg atctggacat tggcctgaat ccgtataaca   5220
gcggaagctt tatcgcgctg tactacacgc acaaaccgaa ctacatcgtc gacatcacgg   5280
acctgatgga actgaaactg aaggcgattc gcgtccatag aagccagttt ccggacgata   5340
tttgggagaa atgggaaccg ttcctgagaa caatcgcgat gttctacggc gaaaaaatcg   5400
gcgttcgcta cggagaaggc tttagaatta tgccgggcct gttctaccac atcacaccgt   5460
ttacggacct gatctgactg cagaagcttg gcgtaatcat ggtcatagct gtttcctgtg   5520
tgaaattgtt atccgctcac aattccacac aacatacgag ccggaagcat aaagtgtaaa   5580
gcctggggtg cctaatgagt gagctaactc acattaattg cgttgcgctc actgcccgct   5640
ttccagtcgg gaaacctgtc gtgccagctg cattaatgaa tcggccaacg cgcgggggaga   5700
ggcggtttgc gtattgggcg ctcttccgct tcctcgctca ctgactcgct gcgctcggtc   5760
gttcggctgc ggcgagcggt atcagctcac tcaaaggcgg taatacggtt atccacagaa   5820
tcagggata acgcaggaaa gaacatgtga gcaaaaggcc agcaaaaggc caggaaccgt    5880
aaaaaggccg cgttgctggc gtttttccat aggctccgcc cccctgacga gcatcacaaa   5940
aatcgacgct caagtcagag gtggcgaaac ccgacaggac tataaagata ccaggcgttt   6000
ccccctggaa gctccctcgt gcgctctcct gttccgaccc tgccgcttac cggataccctg  6060
```

```
tccgcctttc tcccttcggg aagcgtggcg ctttctcata gctcacgctg taggtatctc    6120
agttcggtgt aggtcgttcg ctccaagctg ggctgtgtgc acgaaccccc cgttcagccc    6180
gaccgctgcg ccttatccgg taactatcgt cttgagtcca acccgtaag  acacgactta    6240 tcgccactgg cagcagccac tggtaacagg attagcagag cgaggtatgt aggcggtgct    6300
acagagttct tgaagtggtg gcctaactac ggctacacta agaacagt   atttggtatc    6360 tgcgctctgc tgaagccagt taccttcgga aaaagagttg gtagctcttg atccggcaaa    6420
caaaccaccg ctggtagcgg tggtttttt  gtttgcaagc agcagattac gcgcagaaaa    6480
aaaggatctc aagaagatcc tttgatcttt tctacggggt ctgacgctca gtggaacgaa    6540
aactcacgtt aagggatttt ggtcatgaga ttatcaaaaa ggatcttcac ctagatcctt    6600
ttaaattaaa aatgaagttt taatcaatc  taaagtatat atgagtaaac ttggtctgac    6660
agttaccaat gcttaatcag tgaggcacct atctcagcga tctgtctatt tcgttcatcc    6720
atagttgcct gactcccgt  cgtgtagata actacgatac gggagggctt accatctggc    6780
cccagtgctg caatgatacc gcgagaccca cgctcaccgg ctccagattt atcagcaata    6840
aaccagccag ccggaagggc cgagcgcaga agtggtcctg caactttatc cgcctccatc    6900
cagtctatta attgttgccg ggaagctaga gtaagtagtt cgccagttaa tagtttgcgc    6960
aacgttgttg ccattgctac aggcatcgtg gtgtcacgct cgtcgtttgg tatggcttca    7020
ttcagctccg gttcccaacg atcaaggcga gttacatgat cccccatgtt gtgcaaaaaa    7080
gcggttagct ccttcggtcc tccgatcgtt gtcagaagta agttggccgc agtgttatca    7140
ctcatggtta tggcagcact gcataattct cttactgtca tgccatccgt aagatgcttt    7200
tctgtgactg gtgagtactc aaccaagtca ttctgagaat agtgtatgcg gcgaccgagt    7260
tgctcttgcc cggcgtcaat acgggataat accgcgccac atagcagaac tttaaaagtg    7320
ctcatcattg gaaaacgttc ttcggggcga aaactctcaa ggatcttacc gctgttgaga    7380
tccagttcga tgtaacccac tcgtgcaccc aactgatctt cagcatcttt tactttcacc    7440
agcgtttctg ggtgagcaaa aacaggaagg caaaatgccg caaaaaaggg aataagggcg    7500
acacggaaat gttgaatact catactcttc ctttttcaat attattgaag catttatcag    7560
ggttattgtc tcatgagcgg atacatattt gaatgtattt agaaaaataa acaaataggg    7620
gttccgcgca catttccccg aaaagtgcca cctgacgtct aagaaaccat tattatcatg    7680
acattaacct ataaaaatag gcgtatcacg aggccctttc gtc                      7723
```

<210> SEQ ID NO 5
<211> LENGTH: 47
<212> TYPE: PRT
<213> ORGANISM: Artificial Sequence
<220> FEATURE:
<223> OTHER INFORMATION: Protein translated from synthetic DNA

<400> SEQUENCE: 5

```
Met Ala Lys Pro Leu Ser Lys Gly Gly Ile Leu Val Lys Lys Val Leu
1               5                   10                  15

Ile Ala Gly Ala Val Gly Thr Ala Val Leu Phe Gly Thr Leu Ser Ser
            20                  25                  30

Gly Ile Pro Gly Leu Pro Ala Ala Asp Ala Gln Val Ala Lys Ala
        35                  40                  45
```

<210> SEQ ID NO 6
<211> LENGTH: 30
<212> TYPE: PRT

<213> ORGANISM: Artificial Sequence
<220> FEATURE:
<223> OTHER INFORMATION: Protein translated from synthetic DNA

<400> SEQUENCE: 6

Met Arg Lys Lys Thr Lys Asn Arg Leu Ile Ser Ser Val Leu Ser Thr
1               5                   10                  15
Val Val Ile Ser Ser Leu Leu Phe Pro Gly Ala Ala Gly Ala
            20                  25                  30

<210> SEQ ID NO 7
<211> LENGTH: 28
<212> TYPE: PRT
<213> ORGANISM: Artificial Sequence
<220> FEATURE:
<223> OTHER INFORMATION: Protein translated from synthetic DNA

<400> SEQUENCE: 7

Met Ser Asp Glu Gln Lys Lys Pro Glu Gln Ile His Arg Arg Asp Ile
1               5                   10                  15
Leu Lys Trp Gly Ala Met Ala Gly Ala Ala Val Ala
            20                  25

<210> SEQ ID NO 8
<211> LENGTH: 23
<212> TYPE: PRT
<213> ORGANISM: Artificial Sequence
<220> FEATURE:
<223> OTHER INFORMATION: Protein translated from synthetic DNA

<400> SEQUENCE: 8

Met Lys Lys Gln Arg Met Leu Val Leu Phe Thr Ala Leu Leu Phe Val
1               5                   10                  15
Phe Thr Gly Cys Ser His Ser
            20

<210> SEQ ID NO 9
<211> LENGTH: 26
<212> TYPE: PRT
<213> ORGANISM: Artificial Sequence
<220> FEATURE:
<223> OTHER INFORMATION: Protein translated from synthetic DNA

<400> SEQUENCE: 9

Met Lys Arg Ile Arg Ile Pro Met Thr Leu Ala Leu Gly Ala Ala Leu
1               5                   10                  15
Thr Ile Ala Pro Leu Ser Phe Ala Ser Ala
            20                  25

<210> SEQ ID NO 10
<211> LENGTH: 33
<212> TYPE: PRT
<213> ORGANISM: Artificial Sequence
<220> FEATURE:
<223> OTHER INFORMATION: Protein translated from synthetic DNA

<400> SEQUENCE: 10

Met Phe Ala Lys Arg Phe Lys Thr Ser Leu Leu Pro Leu Phe Ala Gly
1               5                   10                  15
Phe Leu Leu Leu Phe His Leu Val Leu Ala Gly Pro Ala Ala Ala Ser
            20                  25                  30
Ala

```
<210> SEQ ID NO 11
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 11

Met Lys Lys Arg Trp Ser Ile Val Thr Leu Met Leu Ile Phe Thr Leu
1               5                   10                  15

Val Leu Ser Ala
            20

<210> SEQ ID NO 12
<211> LENGTH: 28
<212> TYPE: PRT
<213> ORGANISM: Artificial Sequence
<220> FEATURE:
<223> OTHER INFORMATION: Protein translated from synthetic DNA

<400> SEQUENCE: 12

Met Lys Lys Gly Ile Ile Arg Phe Leu Leu Val Ser Phe Val Leu Phe
1               5                   10                  15

Phe Ala Leu Ser Thr Gly Ile Thr Gly Val Gln Ala
            20                  25

<210> SEQ ID NO 13
<211> LENGTH: 31
<212> TYPE: PRT
<213> ORGANISM: Artificial Sequence
<220> FEATURE:
<223> OTHER INFORMATION: Protein translated from synthetic DNA

<400> SEQUENCE: 13

Met Lys Phe Val Lys Arg Arg Ile Ile Ala Leu Val Thr Ile Leu Met
1               5                   10                  15

Leu Ser Val Thr Ser Leu Phe Ala Leu Gln Pro Ser Ala Lys Ala
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Protein translated from synthetic DNA

<400> SEQUENCE: 14

Met Lys Lys Arg Lys Arg Arg Asn Phe Lys Arg Phe Ile Ala Ala Phe
1               5                   10                  15

Leu Val Leu Ala Leu Met Ile Ser Leu Val Pro Ala Asp Val Leu Ala
            20                  25                  30

<210> SEQ ID NO 15
<211> LENGTH: 27
<212> TYPE: PRT
<213> ORGANISM: Artificial Sequence
<220> FEATURE:
<223> OTHER INFORMATION: Protein translated from synthetic DNA

<400> SEQUENCE: 15

Met Lys Asn Met Ser Cys Lys Leu Val Val Ser Val Thr Leu Phe Phe
1               5                   10                  15

Ser Phe Leu Thr Ile Gly Pro Leu Ala His Ala
            20                  25
```

```
<210> SEQ ID NO 16
<211> LENGTH: 29
<212> TYPE: PRT
<213> ORGANISM: Artificial Sequence
<220> FEATURE:
<223> OTHER INFORMATION: Protein translated from synthetic DNA

<400> SEQUENCE: 16

Met Lys Lys Phe Ala Leu Leu Phe Ile Ala Leu Val Thr Ala Val Val
1               5                   10                  15

Ile Ser Ala Cys Gly Asn Gln Ser Thr Ser Ser Lys Gly
            20                  25

<210> SEQ ID NO 17
<211> LENGTH: 41
<212> TYPE: DNA
<213> ORGANISM: Artificial Sequence
<220> FEATURE:
<223> OTHER INFORMATION: Synthetic DNA

<400> SEQUENCE: 17
agtgatagcg gtaccattat aggtaagaga ggaatgtaca c                    41

<210> SEQ ID NO 18
<211> LENGTH: 114
<212> TYPE: DNA
<213> ORGANISM: Artificial Sequence
<220> FEATURE:
<223> OTHER INFORMATION: Synthetic DNA

<400> SEQUENCE: 18
agtgatagcg gtaccattat aggtaagaga ggaatgtaca catggtcgtc aacatgttcg    60
aggacatcga cacgttcgag gaggtaccat tataggtaag agaggaatgt acac         114
```